United States Patent
Zhang et al.

(10) Patent No.: US 9,952,183 B2
(45) Date of Patent: Apr. 24, 2018

(54) FOCUSING WEDGE FOR ULTRASONIC TESTING

(71) Applicants: Jinchi Zhang, Quebec (CA); C. Tricia Liu, Weston, MA (US); Jason Habermehl, Quebec (CA)

(72) Inventors: Jinchi Zhang, Quebec (CA); C. Tricia Liu, Weston, MA (US); Jason Habermehl, Quebec (CA)

(73) Assignee: Olympus Scientific Solutions America, Waltham, MA (US)

(*) Notice: Subject to any disclaimer, the term of this patent is extended or adjusted under 35 U.S.C. 154(b) by 158 days.

(21) Appl. No.: 14/851,739

(22) Filed: Sep. 11, 2015

(65) Prior Publication Data

US 2017/0074831 A1    Mar. 16, 2017

(51) Int. Cl.
*G01N 29/07* (2006.01)
*G01N 29/28* (2006.01)

(52) U.S. Cl.
CPC ............ *G01N 29/07* (2013.01); *G01N 29/28* (2013.01); *G01N 2291/011* (2013.01); *G01N 2291/0421* (2013.01); *G01N 2291/106* (2013.01)

(58) Field of Classification Search
CPC ............... G01N 29/07; G01N 29/2437; G01N 29/2487; G01N 29/28; G01N 29/326; G01N 29/228; G01F 1/668; G01F 1/662
See application file for complete search history.

(56) References Cited

U.S. PATENT DOCUMENTS

| | | | | | |
|---|---|---|---|---|---|
| 3,663,842 A | * | 5/1972 | Miller | .................... | B06B 1/067 252/62 |
| 3,978,296 A | * | 8/1976 | Moriya | ................... | G04C 3/005 200/4 |
| 4,437,332 A | * | 3/1984 | Pittaro | ................... | G01B 17/02 73/1.82 |
| 4,458,534 A | * | 7/1984 | Kising | ................. | G01N 29/262 73/625 |
| 4,532,796 A | * | 8/1985 | Martens | ................ | G01N 29/22 73/628 |
| 4,545,248 A | * | 10/1985 | Kitada | ................... | G01B 17/02 73/1.81 |

(Continued)

FOREIGN PATENT DOCUMENTS

GB    1285715    8/1972
KR    20090067590    *    6/2009

*Primary Examiner* — Helen Kwok
(74) *Attorney, Agent, or Firm* — C. Tricia Liu

(57) ABSTRACT

Disclosed is a composite focusing wedge for ultrasonic non-destructive testing/inspection. The composite wedge comprises a base made of machined or cast material, and a lens made of a material which is cast in liquid form and subsequently solidifies. The acoustic velocity in the base material is less than that in the lens material. The castable lens material conforms exactly to a convex machined or cast surface of the base, thereby forming a concave lower surface of the lens. A flat ultrasonic probe is coupled to a planar upper surface of the lens. The minimum distance between the lower concave and upper planar surfaces of the lens is less than one acoustic wavelength in the lens material. The ringdown time of reverberations between the two surfaces is then sufficiently short that there is no interference between the reverberations and signals from sub-surface flaws in the object being tested.

20 Claims, 9 Drawing Sheets

(56) References Cited

U.S. PATENT DOCUMENTS

| | | | | |
|---|---|---|---|---|
| 4,658,649 A * | 4/1987 | Brook | ............... | G01N 29/0618 |
| | | | | 73/598 |
| 4,977,780 A * | 12/1990 | Machida | ............... | G10K 11/02 |
| | | | | 600/459 |
| 5,351,546 A * | 10/1994 | Terhune | ............ | G01N 29/2437 |
| | | | | 310/336 |
| 5,477,736 A * | 12/1995 | Lorraine | ............... | G10K 11/30 |
| | | | | 310/335 |
| 5,992,235 A * | 11/1999 | Fischer | ............... | G10K 11/004 |
| | | | | 73/617 |
| 6,065,350 A * | 5/2000 | Hill | ......................... | G01D 5/48 |
| | | | | 73/861.27 |
| 6,349,599 B1 * | 2/2002 | Lynnworth | ......... | G01N 29/223 |
| | | | | 73/644 |
| 8,635,913 B2 * | 1/2014 | Ao | ......................... | G01F 1/662 |
| | | | | 73/644 |
| 8,756,999 B2 * | 6/2014 | Graff | ................ | G01N 29/2487 |
| | | | | 73/632 |
| 2005/0124889 A1 * | 6/2005 | Flesch | ............... | A61B 8/4281 |
| | | | | 600/445 |

\* cited by examiner

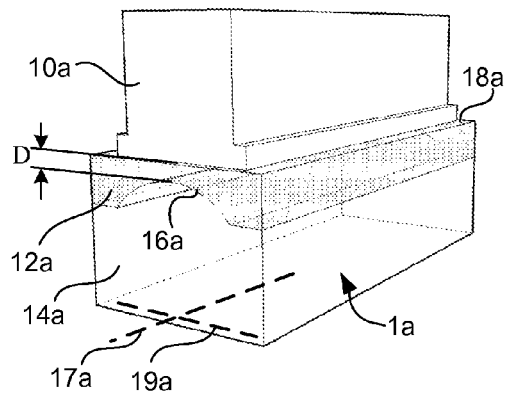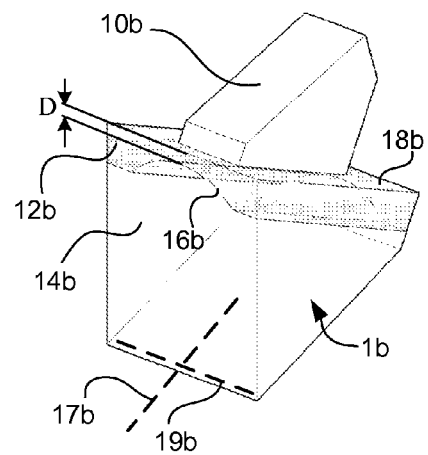
Fig. 1A  Fig. 1B
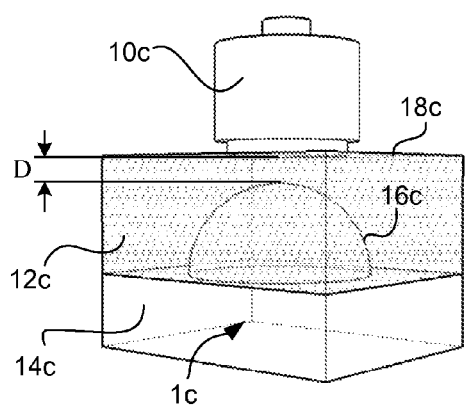
Fig. 1C

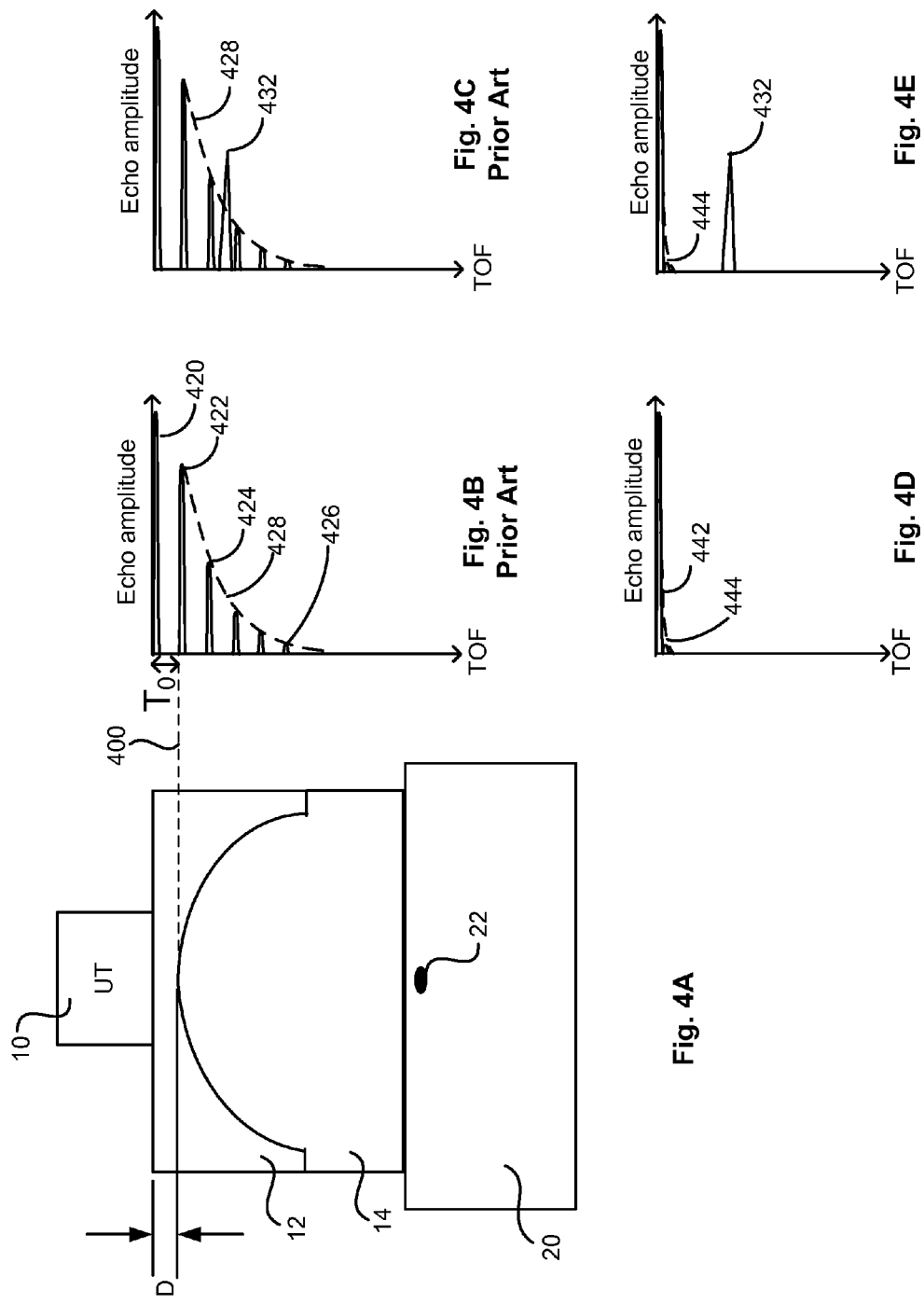

FOCUSING WEDGE FOR ULTRASONIC TESTING

FIELD OF THE INVENTION

The present invention relates to non-destructive testing and inspection systems (NDT/NDI) and more particularly to a composite focusing wedge for use in conjunction with NDT/NDI inspection operations.

BACKGROUND OF THE INVENTION

Beam focalization for ultrasonic transducers has been widely used to concentrate beams of acoustic longitudinal wave (LW) energy from an ultrasonic probe into a particular area of a part to be inspected. Beam focalization can efficiently compensate for energy losses at interfaces and within the part being tested, thereby increasing the signal to noise ratio of the ultrasonic detection and improving the accuracy of flaw sizing. One example of such focalization would be use of an ultrasonic probe to measure corrosion of the inner surface of a pipe. In this case a focused beam from the probe might be used to counteract defocusing at the outer surface of the pipe, in order that the resultant beam would be either parallel or focused on to the inner surface.

One method of focusing the ultrasonic beam is to employ a probe or probe array with a curved surface. The wedge is then manufactured with matching curvature, and the curvature of the probe-wedge interface may be customized in order to achieve the required focal properties. A problem with this approach is that it is difficult to achieve matching curvatures, and if the curvatures are mismatched, the probe surface is prone to be damaged if the probe is tightly screwed to the wedge. Another problem is that it is very expensive to manufacture probes with curved surface, and to customize the curvature for multiple applications. Probes with a flat active surface are much more economical.

Another method of focusing an ultrasonic beam is to use a composite wedge comprising two different materials having different LW velocity, wherein the focusing is achieved at the interface between the two different materials. Patent GB1285715 by Lack describes various combinations of ultrasonic generators and focusing wedges, in which the wedges include a lens made of a material whose acoustic velocity is different from that in the material of the rest of the wedge. However Lack is silent on the question of how such composite wedges may be assembled and how they may be manufactured in large quantities at reasonable cost.

Another problem not addressed by Lack is how to manage reflections of acoustic energy from the interface between the two different materials in the wedge. Reflections from the interface, followed by further reflection at the probe surface, can result in multiple acoustic reverberations which, particularly in cases where a single probe is used as both generator and receiver, can seriously interfere with reception of acoustic signals from flaws in the part being tested.

SUMMARY OF THE INVENTION

One of the objectives of the present disclosure is to provide composite focusing wedges to alleviate problems with prior art composite focusing wedges. In an embodiment, the present disclosure is a wedge comprising a base made of a machined or cast first material with a first acoustic velocity, and a lens made of a second material with a second acoustic velocity. The second material is castable, which means that during manufacturing the second material can be poured into a mold as a liquid which subsequently solidifies or cures into a solid with a second acoustic velocity.

In a preferred embodiment, the upper part of the base is machined as a convex surface, and the lower part of the cast lens is concave and its upper surface is planar. The inventors of the present disclosure have discovered that the problem of reverberations in the composite wedge can be eliminated by making the distance between the concave lower surface and the planar upper surface of the lens as small as possible, namely less than or equal to one wavelength of a longitudinal acoustic wave in the material of the lens.

In another preferred embodiment there is a method enabling the NDT/NDI instrument to identify the type of wedge being used and to set focal laws which are specific to the wedge and to its materials.

It is therefore an objective of the present invention to provide a composite focusing wedge which is capable of mass production at low cost.

It is a further purpose of the present invention to provide a composite focusing wedge in which the matching surfaces of the two parts are reliably conformal, ensuring good transmission of acoustic energy.

It is a further purpose of the present invention to provide a composite focusing wedge in which pockets of air between the matching surfaces of the two parts are eliminated, further ensuring good transmission of acoustic energy. Such air pockets are problematic at the interface of two materials which are glued together.

It is a further purpose of the present invention to provide a composite focusing wedge in which there is reliable adhesion between the two parts, allowing the composite wedge to be free of the complexity of external mechanical fixtures.

It is a further purpose of the present invention to provide a composite focusing wedge in which the reverberations due to reflections at the interface between the two materials do not interfere with signals from sub-surface flaws in the part being inspected.

It is a further purpose of the present invention to provide an NDT/NDI instrument which is capable of identifying the type of the composite wedge in order to apply the correct focal laws to a probe array.

BRIEF DESCRIPTION OF THE DRAWINGS

FIG. 1A is a schematic view of a normal incidence composite wedge with linear focusing according to the present disclosure.

FIG. 1B is a schematic view of an angle beam composite wedge with linear focusing according to the present disclosure.

FIG. 1C is a schematic view of a normal incidence composite wedge with spherical focusing according to the present disclosure.

FIG. 4A illustrates a probe and composite focusing wedge detecting a sub-surface flaw in an object under test.

FIG. 4B shows multiple interface echoes in a prior art composite focusing wedge where the thickness D is much greater than one wavelength of a longitudinal acoustic wave in the material of the lens.

FIG. 4C illustrates prior art detection of a sub-surface flaw with the interface echoes corresponding to FIG. 4B.

FIG. 4D shows interface echoes in a composite focusing wedge according to the present disclosure where the thickness D is less than or equal to one wavelength of a longitudinal acoustic wave in the material of the lens.

FIG. 4E illustrates detection of a sub-surface flaw according to the present disclosure with the interface echoes corresponding to FIG. 4D.

DETAILED DESCRIPTION OF PREFERRED EMBODIMENTS

Figure 2A:
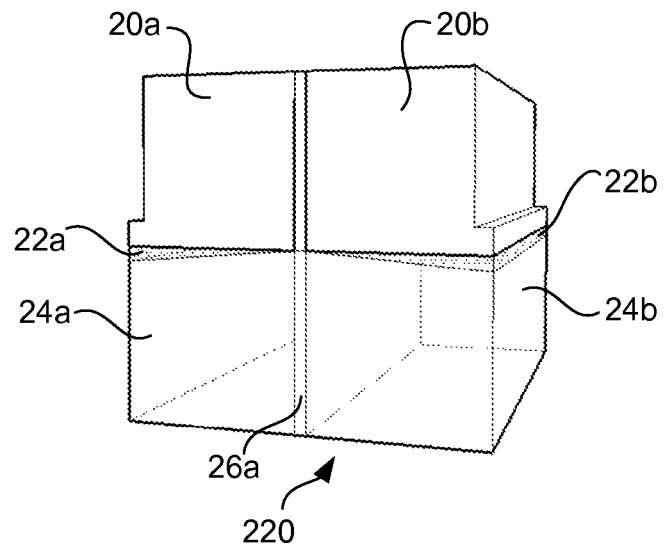
FIG. 2A shows a dual-linear array probe with a composite focusing wedge for flat surface corrosion mapping according to the present disclosure.

FIG. 1A shows a first embodiment which is a normal incidence composite focusing wedge 1a according to the present invention, together with a linear ultrasonic probe 10a. Composite wedge 1a comprises a base 14a, made of a machinable or castable polymer, and a lens 12a, made of a polymer which can be cast in the form of a liquid which subsequently solidifies. Base 14a has a machined or cast curved upper surface 16a, and, after solidification of the polymer, the lower surface of lens 12a is conformal with and adherent to surface 16a. The upper surface 18a of lens 12a is flat, either as cast or as subsequently machined, and D denotes the minimum distance between surface 16a and surface 18a. It should be noted that in the event that linear probe 10a is a phased array linear probe, then a suitable focal law for the phased array can provide focusing along the axis schematically illustrated and denoted by 19a. This axis is known as the active focusing axis for the phased array. On the other hand, the focusing axis of the composite focusing wedge, schematically illustrated and denoted by 17a, is the passive axis of the phased array in which focusing cannot be provided in the absence of a focusing wedge.

FIG. 1B shows a second embodiment which is an angled composite focusing wedge 1b according to the present disclosure, together with an angle beam probe 10b. Composite wedge 1b comprises a base 14b, made of a machinable or castable polymer, and a lens 12b, made of a polymer which can be cast in the form of a liquid which subsequently solidifies. Base 14b has a machined or cast curved upper surface 16b, and, after solidification of the polymer, the lower surface of lens 12b is conformal with and adherent to surface 16b. The upper surface 18b of lens 12b is flat, either as cast or as subsequently machined, and D denotes the minimum distance between surface 16b and surface 18b. Angle beam probe 10b has an active axis 19b and a passive axis 17b.

FIG. 1C shows a third embodiment which is a normal incidence composite focusing wedge 1c with spherical focusing according to the present disclosure, together with a round probe 10c. Composite wedge 1c comprises a base 14c, made of a machinable or castable polymer, and a lens 12c, made of a polymer which can be cast in the form of a liquid which subsequently solidifies. Base 14c has a machined or cast curved upper surface 16c, and, after solidification of the polymer, the lower surface of lens 12c is conformal with and adherent to surface 16c. The upper surface 18c of lens 12c is flat, either as cast or as subsequently machined, and D denotes the minimum distance between surface 16c and surface 18c.

In preferred embodiments, the curved parts of upper surfaces 16a or 16b of bases 14a or 14b respectively are machined or cast to be convex cylindrical, and the LW velocity in the material of lenses 12a or 12b is greater than the LW velocity in the material of bases 14a or 14b respectively, such that wedges 1a or 1b are effective to provide linear focusing in the passive plane of the beams from probes 10a or 10b respectively. In another preferred embodiment, the curved part of upper surface 16c of base 14c is machined or cast to be convex spherical, and the LW velocity in the material of lens 12c is greater than the LW velocity in the material of base 14c, such that wedge 1c is effective to provide spherical focusing of the beam from probe 10c. However it is also within the scope of the invention to machine surfaces 16a, 16b or 16c to be concave, with the LW velocity in the material of lenses 12a, 12b or 12c being less than the LW velocity in the material of bases 14a, 14b or 14c respectively, such that wedges 1a, 1b and 1c are effective to provide focusing.

In the preferred embodiments, the polymer material for lenses 12a, 12b and 12c is 'Tast-setting Acrylic Casting Compound', a product of McMaster Carr Company of Elmhurst, Ill. The product comprises two components, one a powder and the other a liquid, which are cooled to prolong the curing time, then mixed with a ratio of, for example, powder 3:liquid 1. The compound will then self-cure to form a solid Acrylic material in which the LW velocity is 2730 m/s. For a probe of 5 MHz frequency, the LW acoustic wavelength is approximately 0.5 mm, so that the distance D in FIGS. 1A, 1B and 1C should be less than or equal to about 0.5 mm. Also in a preferred embodiment, the polymer material for bases 14a, 14b and 14c is a type of cross-linked polystyrene, in which the LW velocity is 2330 m/s. However, other castable materials for lenses 12a, 12b and 12c and other solid materials for bases 14a, 14b and 14c are possible and are within the scope of the invention.

It should be noted that an important novel aspect of the present invention is the use of castable material to manufacture a composite focusing wedge. The castable lens material, in its initial liquid form, conforms exactly to the machined or cast base of the composite wedge. During the liquid phase, air pockets are eliminated from the interface, ensuring efficient and uniform transmission of ultrasonic energy across the interface. In its final solid form, the castable material adheres strongly to the base, thereby forming a composite wedge which is manufacturable, cost-effective and convenient to use.

Figure 2B:
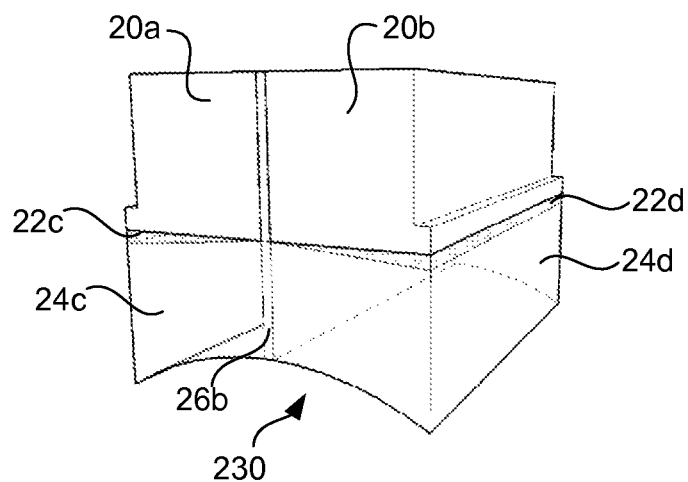
FIG. 2B shows a dual-linear array probe with a composite focusing wedge for convex surface corrosion mapping according to the present disclosure.

The embodiments in FIGS. 1A, 1B and 1C are for use with "pulse-echo" (P-E) mode acoustic testing, in which the same probe is used for generation and sensing of acoustic pulses. FIGS. 2A and 2B illustrate further embodiments of the invention for use with "pitch-catch" (P-C) mode testing, in which acoustic pulses are generated by a first probe and sensed by a second probe. This dual probe configuration has better near surface resolution than the single probe P-E mode configurations illustrated in FIGS. 1A, 1B and 1C.

FIG. 2A illustrates a composite P-C mode wedge 220 for measurement on a flat surface. Wedge 220 comprises bases 24a and 24b, made of a machined or cast polymer, and lenses 22a and 22b, made of a polymer which can be cast in the form of a liquid which subsequently solidifies. Bases 24a and 24b are separated from one another by an acoustic barrier 26a. The bottom surfaces of bases 24a and 24b are flat, suitable for measuring on a flat surface, while the upper surfaces of bases 24a and 24b are machined to a suitable wedge-like shape such that wedge 220 will have the desired focusing properties. After solidification of the polymer, the lower surfaces of lenses 22a and 22b are conformal with and adherent to the machined upper surfaces of bases 24a and 24b. The top surfaces of lenses 22a and 22b are flat and coplanar, either as cast or as subsequently machined. Linear probes 20a and 20b, one of which is a generator and the other a receiver, have flat lower faces which are acoustically coupled to the top surfaces of lenses 22a and 22b.

FIG. 2B illustrates a composite P-C mode wedge 230 for measurement on a convex surface such as a tube. Wedge 230 comprises bases 24c and 24d, made of a machined or cast polymer, and lenses 22c and 22d, made of a polymer which can be cast in the form of a liquid which subsequently solidifies. Bases 24c and 24d are separated from one another by an acoustic barrier 26b. The bottom surfaces of bases 24c and 24d are machined concave, with a shape matching the convex surface to be measured, while the upper surfaces of bases 24c and 24d are machined to a suitable wedge-like shape such that wedge 230 will have the desired focusing properties. After solidification of the polymer, the lower surfaces of lenses 22c and 22d are conformal with and adherent to the machined upper surfaces of bases 24c and 24d. The top surfaces of lenses 22c and 22d are flat and coplanar, either as cast or as subsequently machined. Linear probes 20a and 20b, one of which is a generator and the other a receiver, have flat lower faces which are acoustically coupled to the top surfaces of lenses 22c and 22d. Note that the same probes 20a and 20b with flat faces may be used in the embodiments of both FIG. 2A and FIG. 2B.

The advantage of the dual probe configurations shown in FIGS. 2A and 2B is that the two probe faces can be coplanar, and the focusing depth can be adjusted flexibly by adjusting the composite wedge according to the inspection requirement or the part surface curvature. In many cases, the two probes need to be arranged side by side so closely that it is impossible to have thick edges or side walls between the probes. In this case the two probes are arranged in the same housing and their relative position is fixed. So the focusing depth of the ultrasonic beam needs to be adjusted with the composite wedge.

It should also be noted that, unlike the P-E mode configurations, the dual probe P-C configuration does not suffer from the ringdown problems which will be described later in this disclosure.

In the preferred embodiments, probes 10a, 10b, 20a and 20b are phased-array linear probes. However linear probes of any kind may be used and are within the scope of the invention.

Figure 3A:
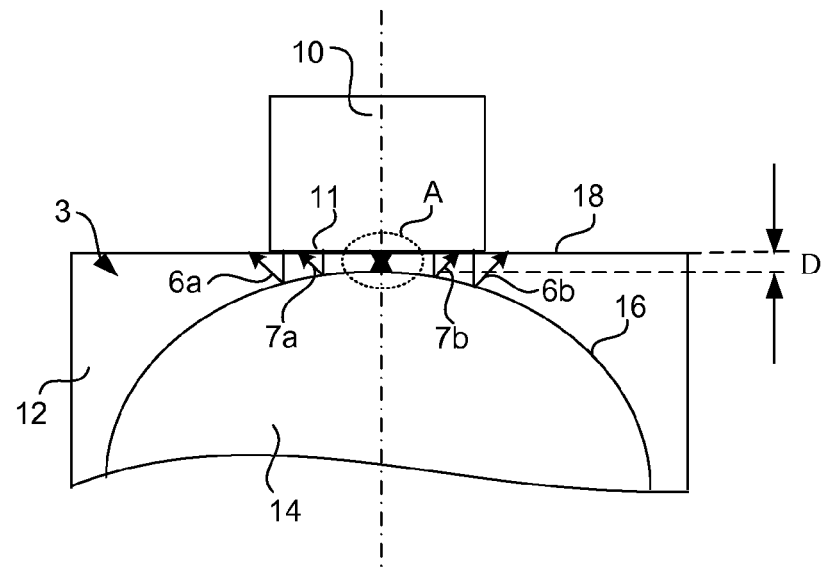
FIG. 3A is a schematic diagram illustrating reverberations in a composite lens.

FIG. 3A illustrates acoustic reverberations in a composite wedge. A composite wedge 3 comprises a machined or cast base 14 and a lens 12 made of castable material. The convex top surface of base 14 forms the interface 16 between base 14 and lens 12. An ultrasonic probe 10 has a flat face 11 which is acoustically coupled to a flat top surface 18 of lens 12. According to the invention, the minimum distance, D, between top surface 18 and interface 16 is less than or equal to one wavelength of a longitudinal acoustic wave in the lens material.

Arrows 6a, 6b, 7a and 7b in FIG. 3A are exemplary illustrations showing how some of the acoustic energy of L-waves generated by probe 10 is reflected by the interface 16. Due to the curvature of interface 16, the reflected energy is directed away from the center of probe 10, and in the case of arrows 6a and 6b, the reflected energy misses probe 10 altogether. In the case of arrows 7a and 7b, the reflections will be sensed as echoes by probe 10. The energy in arrows 7a and 7b may subsequently be reflected from top surface 18, and then again from interface 16, so that it is possible that multiple echoes will be received by probe 10. However, since reflections originating outside the region A in FIG. 3A are always directed away from the center of the probe 10, the number of echoes will be small and will be detected with low sensitivity because of the unfavorable receiving angles.

Figure 3B:
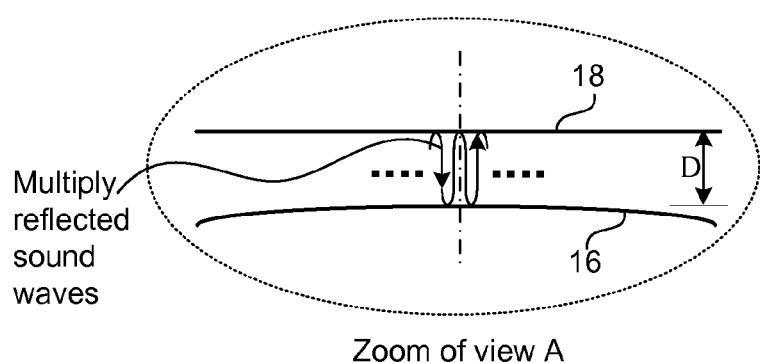
FIG. 3B shows a close-up view of portion A of FIG. 3A

FIG. 3B shows a close-up view of region A. Since region A is close to the center of wedge 3, the curvature of interface 16 is less effective to direct the reflected energy away from the center. As shown in the figure, sound waves are reflected multiple times back and forth between interface 16 and top surface 18, so that probe 10 receives multiple echoes from acoustic pulses originating within region A.

FIG. 4A illustrates a system in which a probe and composite wedge are used to detect a sub-surface flaw 22 in a test object 20. FIGS. 4B, 4C, 4D and 4E are graphs showing the amplitude of the echo signals received by probe 10 as a function of time. "TOF" designates the time of flight of the echo signals.

FIG. 4B shows the signals received in the absence of flaw 22 using a prior art wedge in which the distance D is significantly more than the L-wavelength in the lens material. The "main bang" signal 420 is the echo received coincident with the pulse generated by probe 10. The first echo signal 422 is due to the first reflection of the pulse from interface 16, and the dotted line 400 illustrates schematically that the time $T_0$ between signals 420 and 422 is directly related to the distance D. Second echo signal 424 occurs at time $T_0$ after first echo signal 422, and so on for all subsequent echo signals. The amplitude of subsequent echo signals decays approximately exponentially due to energy losses on reflection at surfaces and within the material of lens 12. The decay envelope 428 is shown as a dotted line, which is commonly referred to as the ringdown envelope. Echo signal 426 is illustrative of the smallest detectable echo signal within the ringdown envelope: in FIG. 4B, signal 426 is shown as the fifth echo signal, but any number of detectable echoes is possible.

FIG. 4C shows the signals from the same prior art wedge as in FIG. 4B, but in the presence of a sub-surface flaw 22. The amplitude of echo signal 432 from sub-surface flaw 22 is barely sufficient to be detected above the amplitude of the ringdown envelope 428, which means that the signal to noise ratio of echo signal 432 will be unfavorable.

FIG. 4D shows the signals received in the absence of flaw 22 using a wedge according to the present disclosure in which the distance D is less than or equal to the L-wavelength in the lens material. Because the distance D is small, the time duration of ringdown envelope 444 is very short, such that in the received signal 442 the main bang and subsequent echoes cannot be resolved from one another.

FIG. 4E shows the signals from the same wedge according to the present disclosure as in FIG. 4D, but in the presence of a sub-surface flaw 22. The echo signal 432 from sub-surface flaw 22 is clearly visible with no background signal from ringdown envelope 444, which means that the signal to noise ratio of echo signal 432 will be favorable.

It should be noted that it is an important and novel aspect of the present invention that reducing the magnitude of the distance D so that it is less than or equal to the L-wavelength enables detection of echo signal 432 with reduced background signal from the ringdown envelope.

It should also be noted that in the foregoing description of exemplary embodiments, the interface between the lens and the wedge base has been illustrated as cylindrical, spherical or wedge-like. It should be appreciated that any other functional interface, which would allow achieving a beam formation in the test object, for example, for improving the distance/gain/size (DGS) flaw sizing with a planar probe fixed on an angled wedge having a planar matching surface, is within the scope of the disclosure.

Figure 5A:
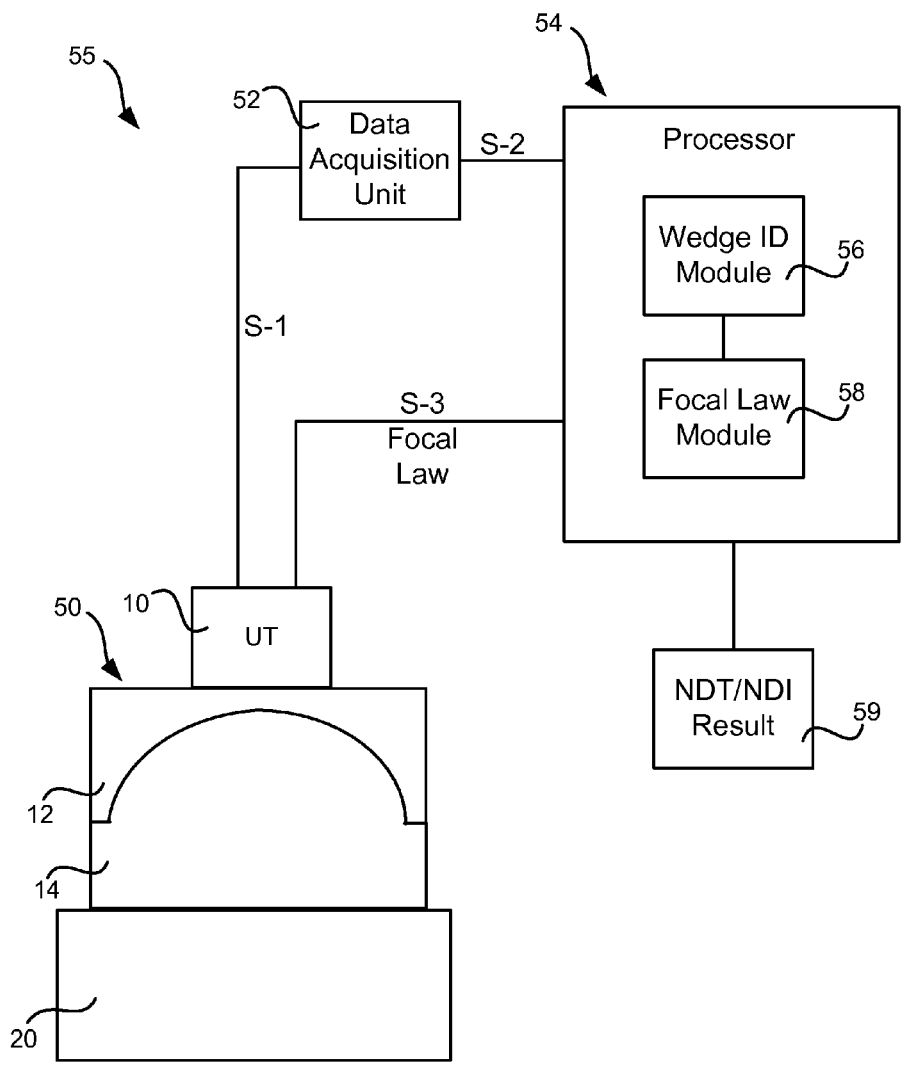
FIG. 5A is a schematic representation of an ultrasonic testing apparatus according to the present disclosure.

FIG. 5A shows a phased array ultrasonic testing and inspection apparatus 55 configured to conduct an inspection session of ultrasonic operation on a test object 20. Inspection apparatus 55 includes a composite focusing wedge 50 with a lens 12 and base 14, and a phased array ultrasonic probe 10 operated by a predetermined focal law generated by a focal law module 58 during the inspection session. A data acquisition unit 52 is electronically coupled with the probe and receives response signals from the probe via signal line S-1. Data from data acquisition unit 52 passes to a processor 54 via signal line S-2. Processor 54 preferably contains a wedge ID module 56 and focal law module 58, both of which are described below in relation to FIG. 5B. Processor 54 produces an NDT/NDI result 59, which may be displayed on an instrument display (not shown).

Figure 5B:
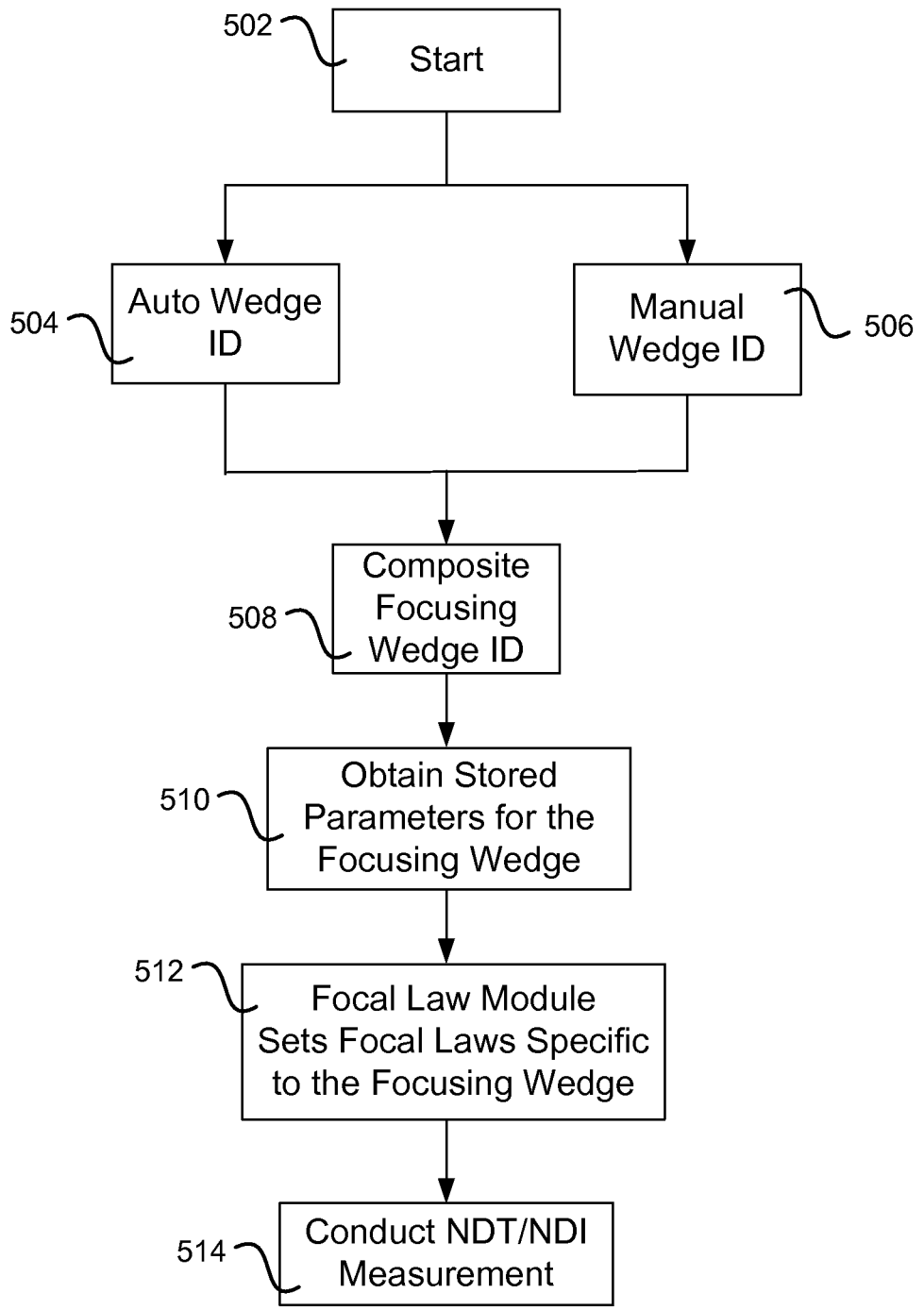
FIG. 5B is a schematic representation of a procedure for a phased array NDT/NDI operation when using the type of the composite focusing wedge according to the present disclosure.

Turning now to FIG. 5B, there is shown a schematic representation of a procedure for a phased array NDT/NDI operation with the type of composite focusing wedge according to the present disclosure. Since different composite focusing wedges will have different focusing properties, all relevant wedge parameters must be obtained by the NDT/NDI instrument in order to apply the correct focal laws to the probe array. Relevant composite wedge parameters include the wedge angle, sound velocity in the base material, sound velocity in the lens material, the shape of the base/lens interface and the height at the middle of the first array element. The parameters for all different wedge types are stored in a computer memory within the NDT/NDI instrument, but in order to access the correct parameters the particular wedge type being used must first be identified. Identification can be done either manually or automatically. Manual identification is based on operator entry of an identifying name or number marked on the wedge. Automatic wedge identification based on time-of-flight measurements is well known in the art.

Accordingly, as shown in FIG. 5B, the operation process begins at step 502, at which point the wedge ID may either be obtained automatically at step 504 or manually at step 506. The known wedge ID at step 508 is used to obtain stored wedge parameters at step 510. The wedge parameters are sent to Focal Law Module 512, which sets appropriate focal laws enabling the NDT/NDI measurement to be conducted in step 514.

Figure 6:
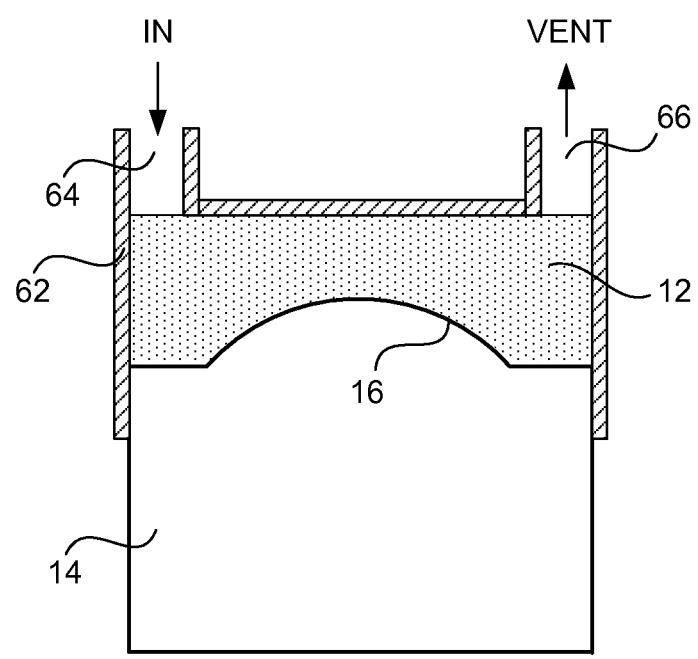
FIG. 6 is a schematic cross-section showing a first embodiment of a composite wedge manufacturing process.
Figure 7A:
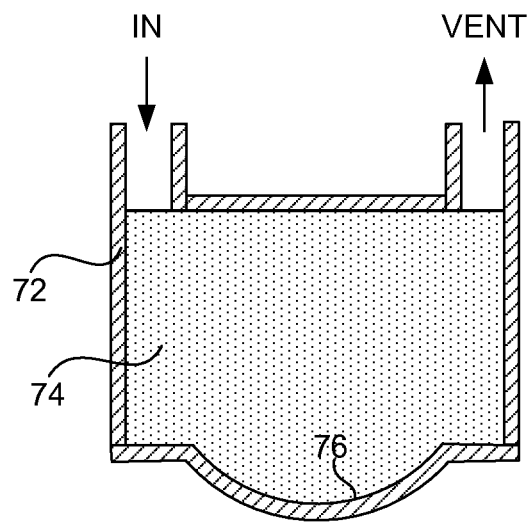
FIGS. 7A and 7B are schematic cross-sections showing two stages of a second embodiment of a composite wedge manufacturing process.
Figure 7B:
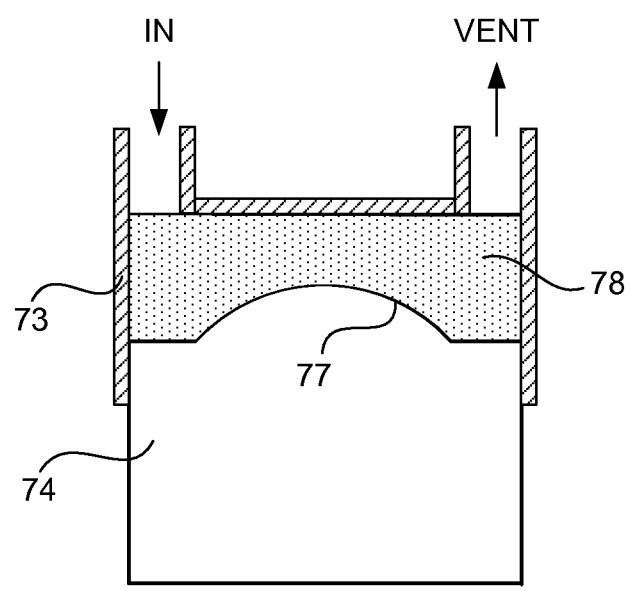
Figure 8A:
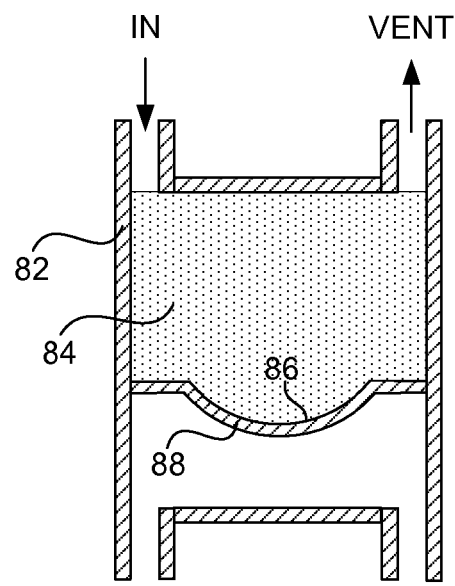
FIGS. 8A and 8B are schematic cross-sections showing two stages of a third embodiment of a composite wedge manufacturing process.

FIGS. 6, 7 and 8 show three embodiments of processes for manufacturing composite focusing wedges according to the present disclosure. It should be noted that in these figures diagonal cross-hatched lines indicate the cross-section of a mold used to contain cast components in their liquid form. After solidification of a cast component, the molds are removed. It should also be noted that in these figures shaded areas refer to components which are in liquid form during the process being described, and which subsequently solidify. Areas which are neither shaded nor cross-hatched refer to components which are solid, except in FIG. 8A where the white space is empty.

In a first embodiment of a manufacturing process, FIG. 6 shows a wedge base 14 made of solid machinable material whose upper surface 16 has been machined to an appropriate shape to attain the desired focusing properties of the completed wedge. A mold 62 is constructed around the base 14, so that the castable material for a lens 12 may be poured into mold 62 through an inlet 64, with allowance for venting of air and vapors via a vent 66.

FIGS. 7A and 7B show a second embodiment of a manufacturing process. In FIG. 7A, a wedge base 74 is made of castable material which is poured into a mold 72 whose lower surface 76 has been machined to an appropriate shape to attain the desired focusing properties of the completed wedge. After solidification and removal of mold 72, wedge base 74 is inverted and in a second manufacturing step shown in FIG. 7B a mold 73 is constructed around the base 74, so that the castable material for a lens 78 may be poured into mold 73. Note that the surface 77 of base 74, which is conformal with surface 76 of mold 72, will form the interface between lens 78 and base 74 in the composite wedge. The advantage of this second embodiment manufacturing process is that the complex machining of the interface surface only needs to be performed once on the mold surface 76, and many bases 74 may be cast thereafter with conformal complex surfaces 77.

Figure 8B:
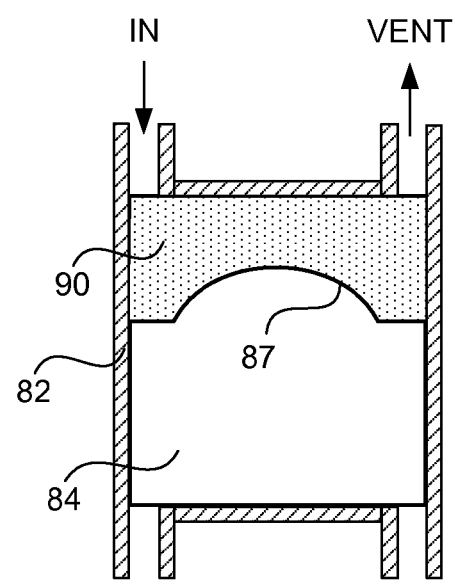

FIGS. 8A and 8B show a third embodiment of a manufacturing process. In FIG. 8A, a wedge base 84 is made of castable material which is poured into a mold 82 with a removable part 88 whose upper surface 86 has been machined to an appropriate shape to attain the desired focusing properties of the completed wedge. After solidification, the entire mold 82 is inverted and removable part 88 is removed, exposing the now solidified surface 87 of wedge base 84, which is conformal with mold surface 86. In a second manufacturing step shown in FIG. 8B, castable material for lens 90 is poured into the other side of mold 82 with the upper surface 87 of solidified wedge base 84 defining the interface of the completed composite wedge. The advantage of this third embodiment manufacturing process is that the complex machining of the interface surface only needs to be performed once on the mold surface 86, and many bases 84 may be cast thereafter with conformal complex surfaces 87.

It should be appreciated that the foregoing description is to disclose teaching, based on the exemplary embodiments, that allows manufacturing a composite focusing wedge using a machined or cast base material and a cast lens material which is conformal with and adherent to a machined or cast curved surface of the base, wherein the LW acoustic velocity is different in the base and lens materials. The teaching also includes a base whose machined or cast surface is convex, and a lens with a concave conformal bottom surface and a planar top surface, wherein the minimum distance D between the concave and planar surfaces is less than or equal to one wavelength of a longitudinal acoustic wave in the material of the lens, thereby preventing reverberations in the lens from interfering with signals from flaws in the part being inspected. Also included is a procedure for identifying the type of focusing wedge to enable application of appropriate focal laws to a probe array. It can be appreciated that various designs can be conceived based on the teachings of the present disclosure, and all are within the scope of the present disclosure.

What is claimed is:

1. A composite focusing wedge used for being mechanically mated with at least one probe, which is electronically coupled to ultrasonic testing and inspection apparatus configured to conduct an inspection session of ultrasonic operation on a testing surface of a test object, the focusing wedge having a probe mating surface intimately mating with the probe and a working surface configured to mate with the testing surface of the test object, the focusing wedge further comprising,
   a first wedge block having one surface to be the probe mating surface, and a second wedge block having one surface to be the working surface, wherein the first block and the second block share an interface having a convex shape with respect to the testing surface,
   wherein the first block is made from a first material having a first sound speed and the second block is made of a second material having a second sound speed,
   wherein the interface is configured so that sound beams originating from the at least one probe, and passing through the composite focusing wedge, are focused on a predetermined area on or below the test surface, and,
   wherein a smallest distance from the probe mating surface to the interface is less than or equal to one wavelength of the sound beams in the first material, thereby improving a signal-to-noise ratio of echo signals from a defect located in the predetermined area.

2. The composite focusing wedge of claim 1, wherein the probe is a phased array probe, and further comprises multiple apertures, each aperture comprises multiple transducer elements, and the interface is configured so that ultrasonic beams emitted from each aperture are guided in a way to be substantially focused onto the predetermined area.

3. The composite focusing wedge of claim 1, wherein the wedge takes a shape of an n-sided prism with the probe mating surface as a prism top, the working surface as a prism bottom, and with the first and the second blocks taking a corresponding shape of the n-sided prism.

4. The composite focusing wedge of claim 3, wherein the wedge is substantially in the shape of a cube, wherein the probe mating surface is parallel to the working surface, and the interface is substantially part of a cylinder, with the axis of the cylinder being parallel to both the probe mating surface and the working surface.

5. The composite focusing wedge of claim 3, wherein the probe mating surface is at an angle to the working surface, and the interface is substantially part of a cylinder, with the axis of the cylinder being parallel to the probe mating surface.

6. The composite focusing wedge of claim 3, wherein the probe mating surface is parallel to the working surface, and there is a center line of rotational symmetry which is perpendicular to both the probe mating surface and the working surface, and wherein the interface is substantially part of a sphere, with the center of the sphere lying on the center line.

7. The composite focusing wedge of claim 1, wherein the composite focusing wedge has a center plane of symmetry which is perpendicular to the probe mating surface, and the wedge is symmetric about the center plane.

8. The composite focusing wedge of claim 7, wherein the at least one probe includes a pair of probes separated along the center plane, the probes are operated in a pitch-catch fashion, and the curvature of the interface is substantially infinitely large.

9. The composite focusing wedge of claim 7, wherein the smallest distance occurs substantially at the center plane.

10. The composite focusing wedge of claim 3, wherein the first material is a machinable solid having a machined surface defining the interface, and the second material can be cast from a mold in the form of a liquid which subsequently solidifies to form the second block.

11. The composite focusing wedge of claim 3, wherein the first and second blocks are cast from molds, the first block forms a first side of the interface conforming to a machined first mold surface of a first mold which defines substantially the interface, and the second block is cast from a second mold and has a second mold surface which conforms to the first side of the interface after solidification.

12. A phased array ultrasonic testing and inspection apparatus configured to conduct an inspection session of ultrasonic operation on a testing surface of a test object, the apparatus comprises,
   at least one phased array ultrasonic probe operated by a predetermined focal law during the inspection session,
   a data acquisition unit electronically coupled with the probe and configured to operate the probe applying the focal law, and receiving response signals from the probe,
   a composite focusing wedge having a probe mating surface in intimate contact with the probe, and a working surface configured to mate to the testing surface of the test object, the focusing wedge further comprising,
   a first wedge block having one surface to be the probe mating surface, and a second wedge block having one surface to be the working surface, wherein the first block and the second block share an interface having a convex shape with respect to the testing surface,
   wherein the first block is made from a first material having a first sound speed and the second block is made of a second material having a second sound speed,
   wherein the interface is configured so that sound beams originating from the at least one probe, and passing through the composite focusing wedge, are focused on a predetermined area on or below the test surface,
   wherein the apparatus is operated with the focal law according to the usage of the focusing wedge, and,
   wherein a smallest distance from the probe mating surface to the interface is less than or equal to one wavelength of the sound beams in the first material, thereby improving a signal-to-noise ratio of echo signals from a defect located in the predetermined area.

13. The inspection apparatus of claim 12, wherein the wedge takes a shape of an n-sided prism with the probe mating surface as a prism top, the working surface as a prism bottom, and with the first and the second blocks taking a corresponding shape of the n-sided prism.

14. The inspection apparatus of claim 13, wherein the wedge is substantially in the shape of a cube, wherein the probe mating surface is parallel to the working surface, and the interface is substantially part of a cylinder, with the axis of the cylinder being parallel to both the probe mating surface and the working surface.

15. The inspection apparatus of claim 13, wherein the probe mating surface is at an angle to the working surface, and the interface is substantially part of a cylinder, with the axis of the cylinder being parallel to the probe mating surface.

16. The inspection apparatus of claim 13, wherein the probe mating surface is parallel to the working surface, and the composite focusing wedge has a center line of rotational symmetry which is perpendicular to both the probe mating surface and the working surface, and wherein the interface is substantially part of a sphere, with the center of the sphere lying on the center line.

17. The inspection apparatus of claim 12, wherein the composite focusing wedge has a center plane of symmetry which is perpendicular to the probe mating surface, and the wedge is symmetric about the center plane.

18. The inspection apparatus of claim 17, wherein the smallest distance occurs substantially at the center plane.

19. The inspection apparatus of claim 13, wherein the first material is a machinable solid having a machined surface defining the interface, and the second material can be cast from a mold in the form of a liquid which subsequently solidifies.

20. The inspection apparatus of claim 13, wherein the first and second blocks are cast from molds, the first block forms a first side of the interface conforming to a machined first mold surface of a first mold which defines substantially the interface, and the second block is cast from a second mold and has a second mold surface which conforms to the first side of the interface after solidification.

* * * * *